United States Patent [19]

Yabumoto et al.

[11] Patent Number: 5,041,990

[45] Date of Patent: Aug. 20, 1991

[54] METHOD AND APPARATUS FOR MEASURING ENTRAINED GAS BUBBLE CONTENT OF FLOWING FLUID

[75] Inventors: Junsuke Yabumoto; Hisashi Yano, both of Kanagawa, Japan

[73] Assignee: Mitsubishi Oil Co., Ltd., Tokyo, Japan

[21] Appl. No.: 424,002

[22] Filed: Oct. 19, 1989

[30] Foreign Application Priority Data

Jan. 10, 1989 [JP] Japan .................. 1-2018

[51] Int. Cl.$^5$ .......................................... G01N 29/00
[52] U.S. Cl. .................... 364/510; 364/558; 73/32 R; 73/53; 73/861.41; 340/603
[58] Field of Search ............. 364/509, 510, 558; 73/32 R, 37, 53, 861.41; 340/603, 606, 611, 609

[56] References Cited

U.S. PATENT DOCUMENTS

| | | | |
|---|---|---|---|
| 4,729,236 | 3/1988 | Samborsky | 364/510 |
| 4,763,525 | 8/1988 | Cobb | 73/599 |
| 4,780,834 | 10/1988 | Craemer et al. | 364/510 |
| 4,956,793 | 9/1990 | Bonne et al. | 364/558 |

FOREIGN PATENT DOCUMENTS 0089098 9/1980 European Pat. Off. .
3210591 3/1982 Fed. Rep. of Germany .

Primary Examiner—Parshotam S. Lall
Assistant Examiner—Brian M. Mattson
Attorney, Agent, or Firm—Sughrue, Mion, Zinn, Macpeak & Seas

[57] ABSTRACT

A method and apparatus measures the gas bubble content of a flowing fluid on a continuous basis without extracting a sample of the fluid. A flowing fluid flows into a density sensor via a temperature and pressure sensor where the temperature, pressure and density of the fluid are determined. As the fluid exits the density sensor, a second pressure sensor determines the pressure of the exiting fluid. The outputs of the sensors are amplified and then input into a data processor. An operating panel supplies required constant data regarding the fluid and gas. The data processor calculates the gas bubble content using the above information in accordance with a predetermined formula.

3 Claims, 2 Drawing Sheets

METHOD AND APPARATUS FOR MEASURING ENTRAINED GAS BUBBLE CONTENT OF FLOWING FLUID

BACKGROUND OF THE INVENTION

The present invention relates to a method and apparatus for measuring the content of gas bubbles entrained in a flowing fluid.

In industrial applications involving the treatment of liquids, such as surfactant solutions, raw material reactants, lubricants, or polymer solutions, it often occurs that air or other gas bubbles are entrained in the fluid due to agitation, stirring or the like. Such entrainment of gas bubbles can lead to difficulties such as inaccurate flow rate measurements, nonuniformity of products, and the generation of noise. Also, in the case of lubricants, such as hydraulic oils, engine oils, turbine oils and the like, there may occur a reduction of hydraulic efficiency and an abnormal amount of wear of the parts to be lubricated.

The conventional approach to determining the content of gas bubbles entrained in such a fluid involves extracting from the flow of fluid a sample of known volume and subsequently weighing the sample or subjecting the sample to gas chromatography. Such methods, however, are disadvantageous because they are time consuming. They are also generally inaccurate due to the possibility of gas escaping from the container holding the sample. Thus, a method of measuring the gas bubble content of a flowing fluid without having to first extract a sample has long been desired.

SUMMARY OF THE INVENTION

Accordingly, an object of the present invention is to provide an in-line measuring method and apparatus for measuring the content of gas bubbles entrained in a flowing fluid.

In accordance with the above and other objects, the invention provides a method and apparatus for measuring the content of gas bubbles entrained in a flowing fluid which operates by detecting the mean density of flowing fluid which contains both liquid and gas bubbles entrained in the liquid.

An apparatus constructed in accordance with the invention for measuring the gas bubble content in a flowing fluid includes a housing, a density sensor for detecting the average density of the flowing fluid, an inside pipe connected to the entrance of the density sensor, another inside pipe connected to the exit of the density sensor, at least one temperature sensor disposed on one of the pipes near the entrance of the density sensor, pressure sensors disposed on the inside pipes near the entrance and exit of the density sensor, means for connecting the inside pipes with outside inlet and outlet pipes, an operation panel for inputting required constant data concerning the fluid, and a data processor receiving the outputs from the density sensor, the temperature and pressure sensors and the constant data from the operation panel for calculating the gas bubble content in response to the received information.

In accordance with the invention, the gas bubble content is calculated employing the following formula:

$$X_0 = \frac{\frac{\rho_l - \rho_m}{\rho_l - \rho_a} \times \frac{273 + t_0}{273 + t} \times \frac{P}{P_0}}{\left(1 - \frac{\rho_l - \rho_m}{\rho_l - \rho_a}\right) \times \frac{VCF(t)}{VCF(t_0)} + \frac{\rho_l - \rho_m}{\rho_l - \rho_a} \times \frac{273 + t_0}{273 + t} \times \frac{P}{P_0}} \times 100$$

wherein:

$X_0$: the gas bubble content by volume percentage in the fluid to be measured at $t_0$ °C. and $P_0$ kg/cm$^2$ Abs.

$\rho_l$: the density of gas-free liquid in g/cm$^3$ at t °C. and P kg/cm$^2$ Abs.

$\rho_a$: the gas density in g/cm$^3$ at t °C. and P kg/cm$^3$ Abs.

$\rho_m$: the average density of the fluid in g/cm$^3$ at t °C. and P kg/cm$^2$ Abs.

$t_0$: normalized temperature in °C.

t: fluid temperature in °C.

$P_0$: normalized pressure in kg/cm$^2$ Abs.

P: average pressure of the fluid in the density sensor, expressed by $P = (P_1 + P_2)/2$ (kg/cm$^2$ Abs.), where $P_1$ and $P_2$ are the respective pressures at the entrance and the exit of the density sensor $VCF(t_0)$: volume correction factor of gas-free liquid at a temperature of $t_0$ °C.

$$VCF(t_0) = \frac{\rho_{l,0}}{\rho_{l,15}}$$

where $\rho_l$, 15 and $\rho_l$, 0 are, respectively, the density of gas-free liquid at temperatures of 15° C. and $t_0$ °C.

VCF (t): volume correction factor of gas-free liquid at a temperature of t ° C.

$$VCF(t) = \frac{\rho_l}{\rho_{l,15}}$$

where $\rho_l$, 15 and $\rho_l$ are, respectively, the density of gas-free liquid at temperatures of 15° C. and t ° C.

DESCRIPTION OF THE PREFERRED EMBODIMENTS

Figure 1:
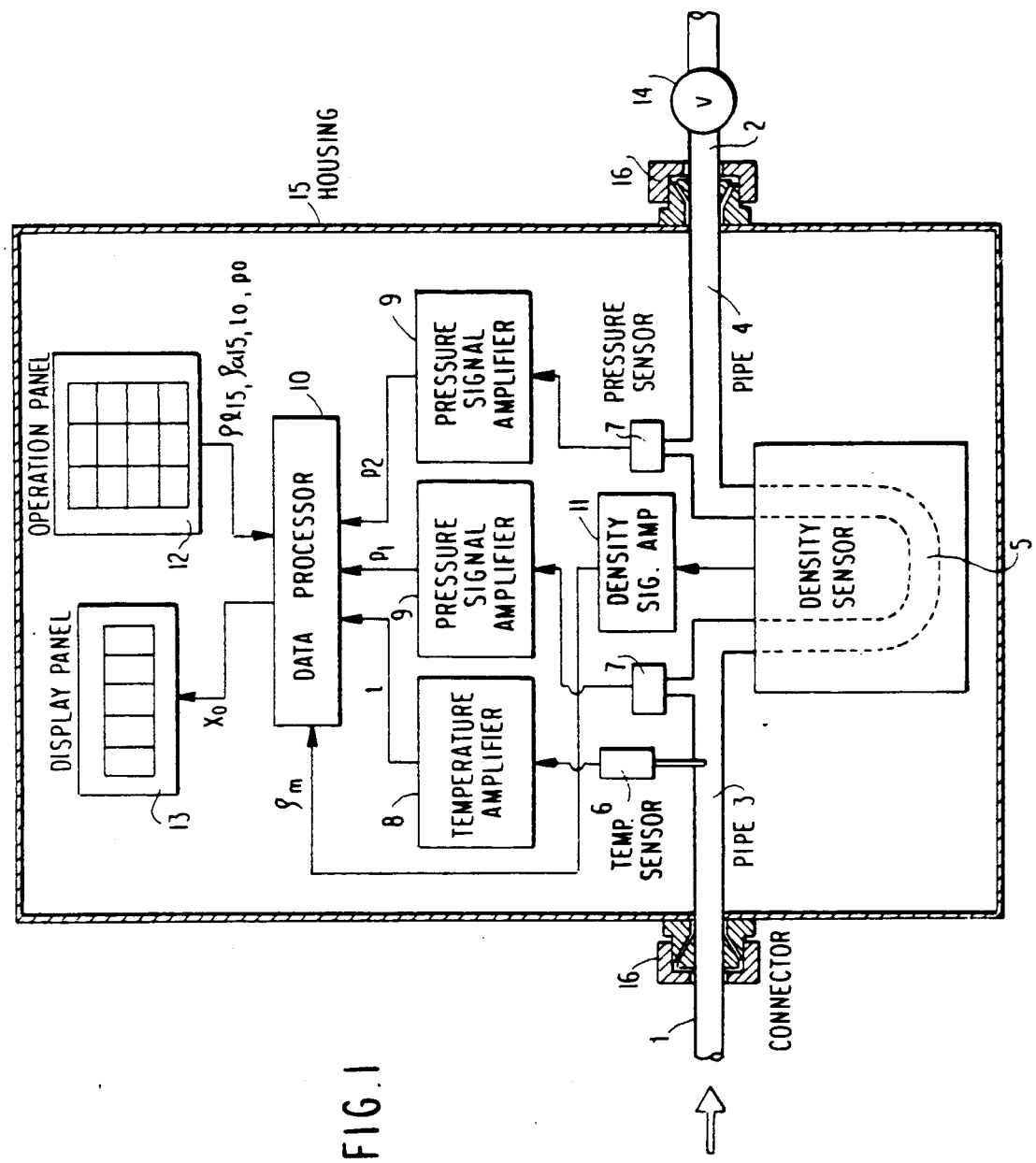
FIG. 1 is a schematic illustration of an apparatus for measuring the content of gas bubbles entrained in a flowing fluid constructed according to the invention.

A preferred embodiment of the invention will be described in detail with reference to FIG. 1, which shows a schematic view of an apparatus of the invention for measuring the content of gas bubbles entrained in a flowing fluid. In this example, it is assumed that the fluid whose gas bubble content is to be measured is an oil.

In this apparatus, an inlet pipe 1 and an outlet pipe 2 are connected via respective inside pipes 3 and 4 to the entrance and exit of a density sensor 5. Connectors 16 join the inlet pipe 1 and the outlet pipe 2 to the respective inside pipes 3 and 4. A temperature sensor 6 is disposed on the inlet-side inside pipe 3 to detect the temperature of the flowing fluid. Two pressure sensors 7 are disposed on respective ones of the inside pipes 3 and 4 just before and after the density sensor 5 to detect the pressures of the flowing fluid at the entrance and exit, respectively, of the density sensor 5. A density signal amplifier 11 receives the output signal from the density sensor 5 and a temperature signal amplifier 8 receives the output signal from the temperature sensor 6, while pressure signal amplifiers 9 receive the output signals from the two pressure sensors 7.

As shown in FIG. 1 a data processor 10 receives the outputs from the density signal amplifier 11, the temperature signal amplifier 8 and the pressure signal amplifiers 9. The data processor 10 is also connected to an operation panel 12 containing source switches, function keys or the like for supplying basic physical data of the gas and liquid concerned. If desired, the operation panel 12 can be used to furnish constant data for the density sensor 5. The operation panel 12 is connected to a display panel 13 for displaying results of calculation, specifically, the bubble content of the gas expressed as a volume percentage, the density of the fluid, the temperature and pressure of the fluid, and other desired parameter.

A valve 14 is disposed on the outlet pipe 2 to adjust the flow rate and the pressure of the fluid.

All of the above-described components, except the inlet pipe 1, outlet pipe 2, connectors 16 and valve 14 are installed in a housing 15.

The fluid whose gas bubble content is to be measured flows in through the inlet pipe 1 and then via the inside pipe 3 to the density sensor. The fluid exits the density sensor 5 and flows out through the inside pipe 4, the outlet pipe 2 and the valve 14.

Figure 2:
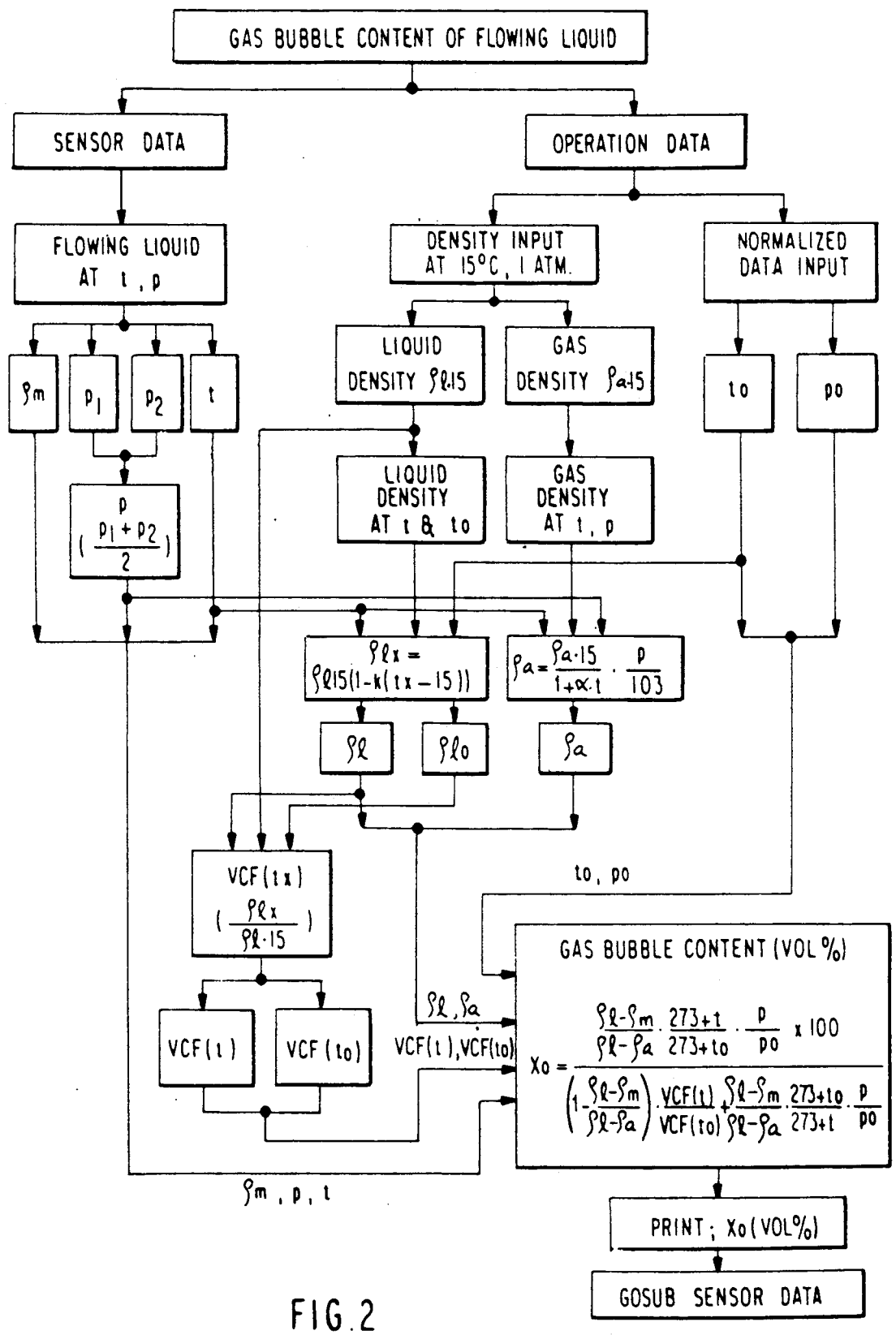
FIG. 2 is a flowchart illustrating the functions performed by the apparatus of FIG. 1 for measuring the content of gas bubbles entrained in a flowing fluid.

In accordance with the invention, the gas bubble content of the gas is calculated by the data processor 10 employing the formula described before, and in accordance with the procedure indicated in the flowchart of FIG. 2.

This completes the description of the preferred embodiment of the invention. Although a preferred embodiment has been described, it is believed that numerous modifications and alterations thereto would be apparent to one of ordinary skill in the art without departing from the spirit and scope of the invention.

What is claimed is:

1. An apparatus for measuring a gas bubble content in a flowing fluid, comprising: a density sensor for detecting an average density of the flowing fluid and outputting said average density to a density signal amplifier for amplifying and outputting said amplified average density; a first inside pipe connected to an entrance of the density sensor; a second inside pipe connected to an exit of the density sensor; a temperature sensor disposed on said first inside pipe near said entrance of said density sensor for outputting a temperature signal of said flowing fluid to a temperature signal amplifier for amplifying and outputting said amplified temperature signal; first and second pressure sensors respectively disposed on said inside pipes near said entrance and exit of said density sensor for respectively outputting first and second pressure signals of said flowing fluid to amplifiers for amplifying and outputting said first and second pressure signals; means for connecting said inside pipes with outside inlet and outlet pipes; means for supplying predetermined constant data; data processing means receiving said outputs of said density signal amplifier, said temperature signal amplifier, said first and second pressure signal amplifiers, and said predetermined constant data for calculating the gas bubble content of said flowing fluid in accordance with said outputs of said density sensor, said temperature sensor, said first and second pressure sensors, and said predetermined constant data; and a housing containing said density sensor, said first and second inside pipes, said temperature sensor, said first and second pressure sensors, and said data processing means.

2. The apparatus of claim 1, wherein said data processing means calculates said gas bubble content of said flowing fluid in accordance with the following formula:

$$X_0 = \frac{\frac{\rho_l - \rho_m}{\rho_l - \rho_a} \times \frac{273 + t_0}{273 + t} \times \frac{P}{P_0}}{\left(1 - \frac{\rho_l - \rho_m}{\rho_l - \rho_a}\right) \times \frac{VCF(t)}{VCF(t_0)} + \frac{\rho_l - \rho_m}{\rho_l - \rho_a} \times \frac{273 + t_0}{273 + t} \times \frac{P}{P_0}} \times 100$$

wherein:

$X_0$: the gas bubble content by volume percentage in the fluid to be measured at $t_0$ °C. and $P_0$ kg/cm$^2$ Abs.

$\rho_l$: density of gas-free liquid in g/cm$^3$ at t °C. and P kg/cm$^2$ Abs.

$\rho_a$: gas density in g/cm$^3$ at t °C. and P kg/cm$^2$ Abs.

$\rho_m$: average density of the fluid in g/cm$^3$ at t °C. and P kg/cm$^2$ Abs.

$t_0$: normalized temperature in °C.

t: fluid temperature in °C.

$P_0$: normalized pressure in kg/cm$^2$ Abs.

P: average pressure of the fluid in the density sensor, expressed by $P = (P_1 + P_2)/2$ (kg/cm$^2$ Abs.), where $P_1$ and $P_2$ are the first and second amplified pressures at the entrance and the exit of the density sensor VCF($t_0$): volume correction factor of gas-free liquid at a temperature of $t_2$ °C.

$$VCF(t_0) = \frac{\rho_{l,0}}{\rho_{l,15}}$$

where $\rho_{l,15}$ and $\rho_{l,0}$ are, respectively, the density of gas-free liquid at temperatures of 15° C. and $t_0$ °C.

VCF(t): volume correction factor of gas-free liquid at a temperature of t °C.

$$VCF(t) = \frac{\rho_l}{\rho_{l,15}}.$$

where $\rho_{l,15}$ and $\rho_l$ are respectively, the density of gas-free liquid at temperatures of 15° C. and t °C.

3. A method for determining a gas bubble content of a flowing fluid, comprising the steps of:

sensing an average density of the flowing fluid at a density sensor;

sensing temperature of the flowing fluid at an entrance of said density sensor;

sensing pressure of said flowing fluid at said entrance and at an exit of said density sensor; and calculating the gas bubble content of said flowing fluid in accordance with the formula:

$$X_0 = \frac{\frac{\rho_l - \rho_m}{\rho_l - \rho_a} \times \frac{273 + t_0}{273 + t} \times \frac{P}{P_0}}{\left(1 - \frac{\rho_l - \rho_m}{\rho_l - \rho_a}\right) \times \frac{VCF(t)}{VCF(t_0)} + \frac{\rho_l - \rho_m}{\rho_l - \rho_a} \times \frac{273 + t_0}{273 + t} \times \frac{P}{P_0}} \times 100$$

wherein:
$X_0$: the gas bubble content by volume percentage in the fluid to be measured at $t_0$ °C. and $P_0$ kg/cm² Abs.

$\rho_l$: density of gas-free liquid in g/cm³ at t °C. and P kg/cm² Abs.

$\rho_a$: gas density in g/cm³ at t °C. and P kg/cm³ Abs.

$\rho_m$: average density of the fluid in g/cm³ at t °C. and P kg/cm² Abs.

$t_0$: normalized temperature in °C.

t: fluid temperature in °C.

$P_0$: normalized pressure in kg/cm² Abs.

P: average pressure of the fluid in the density sensor, expressed by $P = (P_1 + P_2)/2$ (kg/cm² Abs.), where $P_1$ and $P_2$ are the entrance pressure and the exit pressure of the fluid VCF($t_0$): volume correction factor of gas-free liquid at a temperature $t_0$ °C.

$$VCF(t_0) = \frac{\rho_{l,0}}{\rho_{l,15}}$$

where $\rho_{l,15}$ and $\rho_{l,0}$ are, respectively, the density of gas-free liquid at temperature of t °C.

$$VCF(t) = \frac{\rho_l}{\rho_{l,15}}$$

where $\rho_{l,15}$ and $\rho_l$ are, respectively, the density of gas-free liquid at temperatures of 15° C. and t °C., and displaying the calculated gas bubble content.

* * * * *